(12) United States Patent
Atkinson et al.

(10) Patent No.: US 8,778,060 B2
(45) Date of Patent: Jul. 15, 2014

(54) VAPOUR GENERATORS

(75) Inventors: Jonathan Richard Atkinson, Watford (GB); John Patrick Fitzgerald, Watford (GB); Stephen John Taylor, Hyde Heath (GB)

(73) Assignee: Smiths Detection-Watford Limited, Watford (GB)

(*) Notice: Subject to any disclaimer, the term of this patent is extended or adjusted under 35 U.S.C. 154(b) by 0 days.

(21) Appl. No.: 13/424,192

(22) Filed: Mar. 19, 2012

(65) Prior Publication Data
US 2012/0175516 A1 Jul. 12, 2012

Related U.S. Application Data

(63) Continuation of application No. 12/083,151, filed as application No. PCT/GB2006/003677 on Oct. 4, 2006, now Pat. No. 8,137,437.

(30) Foreign Application Priority Data

Oct. 7, 2005 (GB) .................................. 0520397.1

(51) Int. Cl.
*B01D 53/08* (2006.01)

(52) U.S. Cl.
USPC ............ 96/108; 250/282; 250/288; 73/19.01; 73/23.2; 422/88

(58) Field of Classification Search
USPC ...................... 96/108; 422/88; 73/19.01, 23.2; 250/282, 288
See application file for complete search history.

(56) References Cited

U.S. PATENT DOCUMENTS

| | | | |
|---|---|---|---|
| 5,916,133 A | 6/1999 | Buhrmaster et al. | |
| 6,192,766 B1 | 2/2001 | G.ang.rdhagen et al. | |
| 6,627,878 B1 | 9/2003 | Machlinski et al. | |
| 7,399,449 B1 * | 7/2008 | Oborny et al. | ................ 422/504 |
| 2002/0088936 A1 | 7/2002 | Breach et al. | |

FOREIGN PATENT DOCUMENTS

EP 0 447 158 A 9/1991
WO WO-2004/092704 A 10/2004

OTHER PUBLICATIONS

Office Action in U.S. Appl. No. 12/083,151 dated Jun. 8, 2011.

* cited by examiner

*Primary Examiner* — Robert A Hopkins
(74) *Attorney, Agent, or Firm* — Foley & Lardner LLP

(57) ABSTRACT

A vapor generator system (1, 101) for an IMS (4, 104) or other apparatus has a chamber (9, 109) in which vapor is produced. A fan or other flow generator (6, 106) is connected to an inlet (8, 108) of the vapor chamber (9, 109) and its outlet (13, 113) is connected to an adsorbent passage (14, 114), such as formed by a bore through a block (15) of carbon. When the fan (6, 106) is on gas flows through the vapor chamber (9, 109) and the adsorbent passage (14, 114) to the IMS (4, 104) or other outlet, with little vapor being adsorbed in the passage. When the fan (6, 106) is off, any vapor molecules that escape to the adsorbent passage (14, 114) do so at a low rate such that substantially all is adsorbed and no vapor escapes.

28 Claims, 1 Drawing Sheet

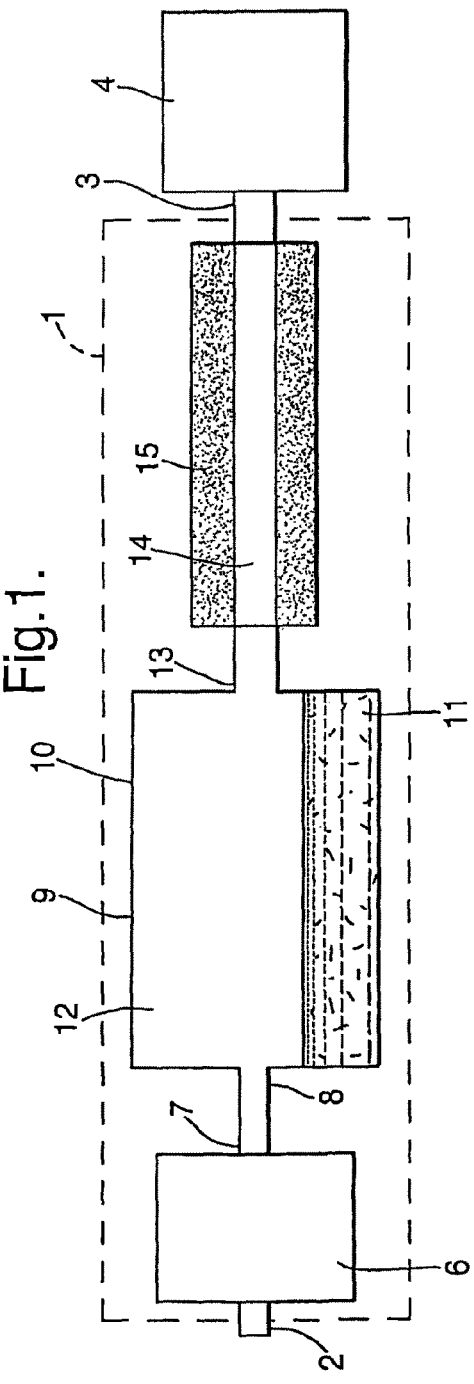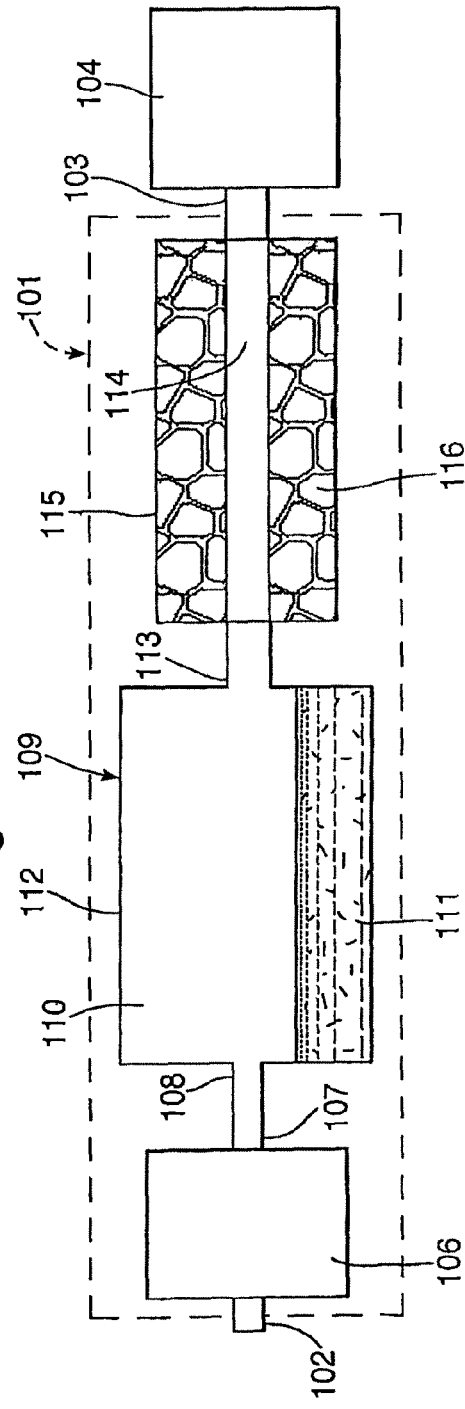

VAPOUR GENERATORS

This invention relates to vapour generators of the kind including a chamber in which a vapour is produced, an inlet by which gas can enter the chamber, and a chamber outlet by which vapour can flow out of the chamber.

There are many applications where it is necessary to generate vapour. For example, ion mobility spectrometers and other detectors often include a vapour generator to supply a dopant chemical to the equipment. Vapour generators can also be used to supply a test chemical for use in testing or calibrating a detector, a filter or other equipment. In some applications it is important to be able to switch the vapour generator on and off rapidly and to prevent leakage when the detector is off. In an IMS system this would enable rapid switching between different doping conditions, such as different levels of dopant or different dopant substances. It could also enable different regions of IMS apparatus to be doped differently by ensuring there was no leakage to undoped regions of the apparatus when the apparatus is switched off.

One technique of reducing leakage of vapour has been employed in an explosives detector produced by Graseby Dynamics Limited of Watford, England under the PD5 name. In this, a container of adsorbent material is connected at an outlet of a vapour generator via a T-junction. When the vapour generator is off and there is a nominal zero flow, some of the residual vapour produced passes via one arm of the T-junction to the adsorbent material. When the generator is turned on, the gas flow through it rises high enough to ensure that most of the vapour is carried through the other arm of the T-junction to the outlet. The problem with this arrangement is that the vapour can easily by-pass the adsorbent material leading to a relatively low adsorption efficiency and relatively high levels of escaped vapour.

It is an object of the present invention to provide an alternative vapour generator, detection system and method of generating vapour.

According to one aspect of the present invention there is provided a vapour generator of the above-specified kind, characterised in that the generator includes a vapour-adsorbent passage extending from the chamber outlet such that all gas and vapour flowing from the chamber outlet flows through the vapour-adsorbent passage and such that, when no gas is caused to flow through the generator, vapour produced in the chamber flows to the passage and is adsorbed at a rate that ensures substantially no vapour passes as far as the generator outlet but, when gas is caused to flow through the generator, the vapour is carried through the passage at a rate sufficiently high to ensure a flow of vapour from the generator outlet.

The passage may be provided through an adsorbent material, such as a sintered material. Alternatively, the passage may be provided by a vapour-permeable passage extending through adsorbent means, which may include a chamber containing a adsorbent material, such as including charcoal. The vapour-permeable passage may be provided by vapour-permeable tubing, such as of an elastomer. The vapour generator preferably includes an airflow generator connected with the inlet of the vapour chamber. The airflow generator may be a fan of blower.

According to another aspect of the present invention there is provided a detection system including detection apparatus and a vapour generator according to the above one aspect of the invention arranged to supply vapour to the detection apparatus.

The detection apparatus may include an IMS or gas chromatography instrument.

According to a further aspect of the present invention there is provided a method of controlling the production of vapour, including the steps of causing a flow of gas through a vapour source to a vapour-adsorbent passage at a rate sufficient to ensure that vapour flows out of the passage, and terminating the flow of gas such that any vapour from the source entering the passage is adsorbed thereby at a rate sufficient to ensure that substantially no vapour flows out of the passage.

A system of a vapour generator for use in supplying vapour to an IMS detector will now be described, by way of example, with reference to the accompanying drawing, in which:

FIG. 1 shows the system schematically; and
FIG. 2 shows a modified system schematically.

With reference first to FIG. 1, the vapour generator 1 has an air inlet 2 and a vapour outlet 3 connected to an inlet of an IMS detector 4. The vapour generator 1 is used to provide a readily controllable supply of a dopant vapour to the IMS 4 and, it will be appreciated that the generator would normally be contained within the same housing as the IMS. The vapour generator could be used in conjunction with other detectors such as gas chromatography instruments. The vapour generator could also be used for calibration purposes within the instrument.

The generator 1 has a airflow generator 6 in the form of a fan, blower or the like connected at the inlet 2. This can be switched on or off to provide a flow of air to its outlet 7 as desired. The airflow generator 6 could include various filters or other devices to remove contaminants and water vapour from atmospheric air before this is supplied to the outlet 7. Alternative gas flow generators could be used, such as provided by a container of compressed gas, which need not be air.

The outlet 7 of the airflow generator 6 connects with the inlet 8 at one end of a vapour chamber 9. The vapour chamber 9 may take many different forms but, in this example, comprises a housing 10 containing a wicking, adsorbent material 11 soaked with a compound in its liquid phase, such as acetone, so that the space 12 above the material is filled with the vapour of the liquid at its saturated vapour pressure at the ambient temperature. The vapour chamber 9 has an outlet 13 at its opposite end through which vapour and air can flow out of the chamber. Vapour-producing substances other than acetone could be used.

The vapour chamber outlet 13 connects with one end of a vapour-adsorbent passage 14. In the present example, this passage 14 is provided by a machined bore or slot through a block 15 of carbon or a sintered material, such as a molecular sieve material, which could be of zeolite as described in PCT/GB06/001440. Alternatively, the passage through the block could be formed by moulding the block about a core pin that is subsequently removed to leave a bore or passage through the block. The material of the block is adsorbent of the acetone vapour. The material itself could be adsorbent, such as of carbon, or the material itself could be non-adsorbent but could be rendered adsorbent by impregnation with a suitable substance. In this way, acetone vapour is adsorbed by the block at all locations along the passage. The outlet end of the passage 14 connects with the vapour outlet 3.

When the vapour generator 1 is off, that is, when no flow of vapour is needed, the airflow generator 6 remains unenergised so that there is no flow of air through the vapour chamber 9 and the adsorbent passage 14. The passage 14 is, however, open to the interior 12 of the vapour chamber 9 so some vapour will drift into the tube. As it does so, it diffuses into the block 15 and is adsorbed therein. The bore, length, porosity and nature of the material of the block 15 are chosen such that, under zero flow conditions, the amount of vapour that escapes from the outlet end of the passage 14 is insignificant in the context of the application in which the vapour generator is used. In the present example, where the vapour generator is used as a dopant source in an IMS system 4, the vapour dopant flow in the off state is arranged to be not sufficient to produce any noticeable dopant ion peak in the IMS apparatus.

The generator 1 is turned on to produce a flow of vapour at its outlet 3 by turning on the airflow generator 6 to produce a flow of air into the inlet 8 of the vapour chamber 9. This flow collects the vapour produced in the vapour chamber 9 and pushes it through the outlet 13 and into the passage 14. The flow velocity in the passage 14 is chosen such that the residence time of the collected vapour in the passage is sufficiently low that little is adsorbed into the block material. Thus, a large proportion of the vapour arrives at the open, outlet end of the passage 14 and at the outlet 3 of the generator and is delivered to the IMS apparatus 4. This flow can be continuous or pulsed.

The vapour generator 1 is able to turn off vapour flow very rapidly when not required, such that its vapour does not leak out at a significant rate. In an IMS system, this effectively prevents dopant vapour from entering the IMS apparatus when the system is turned off and is not powered. This can enable selected regions of IMS apparatus to be doped with a reduced risk that dopant will leak to undoped regions when the apparatus is turned off. In conventional systems, gas flow through the IMS apparatus can keep undoped regions free of dopant when the apparatus is powered but, when not powered, the gas flow ceases and any slight leakage of dopant will contaminate all regions of the apparatus. This has previously made it very difficult to dope different regions of IMS apparatus differently except where the apparatus is continuously powered.

The generator could include alternative means for adsorbing the vapour. FIG. 2 shows an alternative arrangement in which components equivalent to those in the arrangement shown in FIG. 1 have been given the same reference numerals with the addition of 100.

The generator 101 has the same airflow generator 106 and vapour chamber 109 as in the arrangement of FIG. 1. Instead of a block of adsorbent material, an adsorbent passage 114 is provided by a length of a small bore tube of an elastomeric plastics such as silicone rubber. The tube 114 is approximately 100 mm long with an external diameter of approximately 1 mm and an internal diameter of approximately 0.5 mm. The entire length of the tube 114 is enclosed within an outer cylindrical housing 115 of a vapour-impermeable material, the tube extending axially along the centre of the housing. The space between the outside of the tubing 114 and the inside of the housing 115 is filled with a material 116 that readily adsorbs the vapour produced. In the present example, the material is in the form of charcoal granules 116, which are effective to adsorb acetone vapour. The tube 114 is surrounded on all sides by the adsorbent charcoal granules 16 and its outlet end connects with the vapour outlet 103.

The bore, length, wall thickness and material of the tube 114 are chosen such that, under zero flow conditions, the amount of vapour that escapes from the outlet end of the tube is insignificant in the context of the application in which the vapour generator is used.

Instead of the airflow generator being at the inlet of the vapour chamber to pump air into the chamber, the airflow generator could be connected downstream of the vapour chamber and be arranged to suck air into the chamber. The airflow generator could be connected between the outlet of the vapour chamber and the inlet end of the adsorbent passage, or it could be connected downstream of the adsorbent passage, at the outlet end of the passage. The disadvantage of this alternative arrangement is that the airflow generator would be exposed to the vapour but this might not matter in some applications.

The generator could include a pneumatic valve connected to block flow of vapour from the vapour chamber to the adsorbent passage until vapour flow was needed. This would have the advantage of preventing continual adsorption of the vapour into the adsorbent material and lengthen the life of both the vapour chamber and the adsorbent material. The adsorbent passage would only have to trap vapour that permeates through the valve seal so, with this arrangement, there would be a lower rate of diffusion and the length of the adsorbent passage could be reduced.

A second adsorbent arrangement could be connected between the inlet of the vapour chamber and the airflow generator to prevent vapour from the chamber passing to the airflow generator in significant quantities when the flow was off. A pneumatic valve could be connected between this second adsorbent passage and the vapour chamber, the valve being maintained closed until flow was required.

The whole arrangement of the vapour chamber, adsorbent passages and valves could be buried in a bed of charcoal or other adsorbent material to ensure that vapour could not escape from the apparatus in the off state.

The arrangement of the present invention provides a very efficient trapping of vapour. The vapour generator is not confined to use in doping detectors but could be used in other applications. For example, the vapour generator could be used to provide a periodic internal calibrant material in a detection system. The detection system could be an IMS detector, gas chromatograph system, mass spectrometer or other system. The generator could be used for calibration or testing of other detectors, filters or the like.

What is claimed is:

1. An apparatus comprising:
   a vapor adsorbent passage configured to receive air that includes a dopant vapor usable to aid in identification of an unknown substance,
   wherein, when the apparatus is in an on configuration, the vapor adsorbent passage allows the dopant vapor to flow through the passage at a velocity such that at least some of the dopant vapor flows out of the vapor adsorbent passage, and
   wherein, when the apparatus is in an off configuration, the vapor adsorbent passage adsorbs substantially all dopant vapor that drifts into the vapor adsorbent passage, such that substantially no dopant vapor flows out of the vapor adsorbent passage.

2. The apparatus of claim 1, wherein the vapor adsorbent passage is configured to operate at ambient conditions.

3. The apparatus of claim 1, wherein the vapor adsorbent passage includes carbon or a sintered material.

4. The apparatus of claim 1, wherein the vapor adsorbent passage includes molecular sieve material.

5. The apparatus of claim 1, further comprising an airflow generator configured to generate a flow of air through the vapor adsorbent passage.

6. The apparatus of claim 1, wherein the vapor adsorbent passage is configured to deliver a pulse of the dopant vapor in the on configuration.

7. The apparatus of claim 1, wherein in the off configuration, any dopant that exits from the vapor passage is insufficient for a detector to detect a noticeable ion peak associated with the dopant.

8. The apparatus of claim 1, wherein the vapor passage in an on configuration is configured to dope a first region of an ion-mobility spectrometry device without doping a second region of the ion-mobility spectrometry device.

9. An apparatus comprising:
a vapor passage configured to adsorb a dopant usable to aid in identification of an unknown substance, the vapor passage being operable to flow air that includes the unknown substance and the dopant to a detector in an on configuration and substantially prevent dopant from desorbing from the vapor passage in an off configuration
wherein the vapor passage comprises a vapor-permeable elastic tubing.

10. A method comprising:
providing a vapor generator comprising:
a vapor chamber configured to produce a dopant vapor usable to aid in identification of an unknown substance, and
a vapor adsorbent passage connected to the vapor chamber in a manner such that air that includes the dopant vapor is passable from the vapor chamber to the vapor adsorbent passage;
placing the vapor generator in an on configuration in which the vapor adsorbent passage allows the dopant vapor to flow through the passage at a velocity such that at least some of the dopant vapor flows out of the vapor adsorbent passage, and
placing the vapor generator in an off configuration in which the vapor adsorbent passage adsorbs substantially all dopant vapor that drifts into the vapor adsorbent passage from the vapor chamber, such that substantially no dopant vapor flows out of the vapor adsorbent passage.

11. The method of claim 10, wherein the flow of air through the vapor adsorbent passage is rapidly terminable by ceasing operation of an airflow generator, so as to provide power savings when the vapor is not needed.

12. The method of claim 10, wherein the flow of air through the vapor adsorbent passage) The method of claim 10, wherein the vapor adsorbent passage is configured to operate at ambient conditions.

13. The method of claim 10, wherein the vapor adsorbent passage includes carbon or a sintered material.

14. The method of claim 10, wherein the vapor adsorbent passage includes molecular sieve material.

15. The method of claim 10, wherein the vapor adsorbent passage is placed in the on configuration by generating a flow of air through the vapor adsorbent passage, and the vapor adsorbent passage is placed in the off configuration by terminating the flow of air through the vapor adsorbent passage.

16. The method of claim 10, further comprising delivering a pulse of the dopant vapor during the operation of the vapor adsorbent passage.

17. The method of claim 10, when the operation of the vapor adsorbent passage is terminated, any dopant that exits from the vapor adsorbent passage is insufficient for a detector to detect a noticeable ion peak associated with the dopant.

18. The method of claim 10, wherein the vapor passage in an on configuration is configured to dope a first region of an ion-mobility spectrometry device without doping a second region of the ion-mobility spectrometry device.

19. A method comprising:
operating a vapor passage to flow air that includes an unknown substance and a dopant to a detector; and terminating operation of the vapor passage to prevent dopant from desorbing from the vapor passage,
wherein the vapor passage comprises a vapor-permeable elastic tubing.

20. A system comprising:
an ion-mobility spectrometry device; and
a vapor generator comprising:
a vapor chamber configured to produce a dopant vapor usable to aid in identification of an unknown substance,
a vapor adsorbent passage connected to the vapor chamber in a manner such that air that includes the dopant vapor is passable from the vapor chamber to the vapor adsorbent passage, and
an airflow generator configured to pulse the flow of air through the vapor passage,
wherein, when the vapor generator is in an on configuration, the vapor adsorbent passage allows the dopant vapor to flow through the passage at a velocity such that at least some of the dopant vapor flows out of the vapor adsorbent passage to the ion-mobility spectrometry device, and
wherein, when the vapor generator is in an off configuration, the vapor adsorbent passage adsorbs substantially all dopant vapor that drifts into the vapor adsorbent passage from the vapor chamber, such that substantially no dopant vapor flows out of the vapor adsorbent passage to the ion-mobility spectrometry device.

21. The system of claim 20, wherein the flow of air through the vapor adsorbent passage is rapidly stoppable by ceasing operation of the airflow generator, so as to provide power savings when the flow of air is not needed in the ion-mobility spectrometry device.

22. The system of claim 20, wherein the vapor adsorbent passage is configured to operate at ambient conditions.

23. The system of claim 20, wherein the vapor adsorbent passage includes carbon or a sintered material.

24. The system of claim 20, wherein the vapor adsorbent passage includes molecular sieve material.

25. The system of claim 20, wherein in the off configuration, any dopant that exits from the vapor adsorbent passage is insufficient for the ion-mobility spectrometry device to detect a noticeable ion peak associated with the dopant.

26. The system of claim 20, wherein the vapor adsorbent passage in an on configuration is configured to dope a first region of the ion-mobility spectrometry device without doping a second region of the ion-mobility spectrometry device.

27. The system of claim 20, wherein the vapor adsorbent passage is separated from the vapor chamber by a valve that is selectively operable to block a flow of air from the vapor chamber to the vapor adsorbent passage.

28. A system comprising:
an ion-mobility spectrometry device;
a vapor passage configured to adsorb a dopant usable to aid in identification of an unknown substance, the vapor passage being operable to flow air that includes the unknown substance and the dopant to the ion-mobility spectrometry device in an on configuration and substantially prevent dopant from desorbing from the vapor passage in an off configuration; and
an airflow generator configured to pulse the flow of air through the vapor passage,
wherein the vapor passage comprises a vapor-permeable elastic tubing.

* * * * *